United States Patent
Sacharoff et al.

(10) Patent No.: US 8,231,673 B2
(45) Date of Patent: Jul. 31, 2012

(54) NON-INVASIVE POWER ADJUSTABLE INTRAOCULAR LENS

(75) Inventors: Alex Sacharoff, Oviedo, FL (US); Mutlu Karakelle, Fort Worth, TX (US)

(73) Assignee: Novartis AG, Basel (CH)

( * ) Notice: Subject to any disclaimer, the term of this patent is extended or adjusted under 35 U.S.C. 154(b) by 397 days.

(21) Appl. No.: 12/434,237

(22) Filed: May 1, 2009

(65) Prior Publication Data
US 2009/0281620 A1    Nov. 12, 2009

Related U.S. Application Data

(60) Provisional application No. 61/050,913, filed on May 6, 2008.

(51) Int. Cl.
*A61F 2/16* (2006.01)
(52) U.S. Cl. ..................................................... 623/6.22
(58) Field of Classification Search ........ 623/6.11–6.12, 623/6.22, 6.37, 6.43, 6.46
See application file for complete search history.

(56) References Cited

U.S. PATENT DOCUMENTS

| | | | | |
|---|---|---|---|---|
| 4,575,373 A | * | 3/1986 | Johnson | 623/6.22 |
| 5,571,177 A | * | 11/1996 | Deacon et al. | 623/6.47 |
| 2004/0169932 A1 | | 9/2004 | Esch et al. | |
| 2005/0137703 A1 | | 6/2005 | Chen | |
| 2006/0116764 A1 | * | 6/2006 | Simpson | 623/6.23 |
| 2007/0182924 A1 | | 8/2007 | Hone et al. | |

FOREIGN PATENT DOCUMENTS
WO    WO 92/03989    3/1992

* cited by examiner

*Primary Examiner* — William H. Matthews
(74) *Attorney, Agent, or Firm* — Jonathan E. Prejean

(57) ABSTRACT

An improved multifocal design for an ocular implant is provided. This ocular implant includes an intraocular lens (IOL) and a number of haptics. The IOL passes optical energy. A microstructure within the IOL places the IOL under tension. The microstructure is operable to be broken in a controlled manner to release tension in the IOL and reshape the IOL. This may be done at any time post operatively and in conjunction with wavefront aberrometry to provide improved results. The haptics mechanically couple to the IOL in order to position and secure the IOL within the eye.

13 Claims, 6 Drawing Sheets

NON-INVASIVE POWER ADJUSTABLE INTRAOCULAR LENS

RELATED APPLICATIONS

This application claims priority to U.S. provisional application Ser. No. 61/050,913, filed on May 6, 2008, the contents which are incorporated herein by reference.

TECHNICAL FIELD OF THE INVENTION

The present invention relates generally to the human eye and more particularly to intraocular lenses (IOLs).

BACKGROUND OF THE INVENTION

The human eye in its simplest terms functions to provide vision by transmitting light through a clear outer portion called the cornea, and focusing the image by way of a lens onto a retina. The quality of the focused image depends on many factors, including the size and shape of the eye, and the transparency of the cornea and lens. Age and/or disease often cause the lens to become less transparent. Thus, vision deteriorates because of the diminished light which can be transmitted to the retina. This deficiency in the lens of the eye is medically known as a cataract.

An accepted treatment for this condition is surgical removal of the lens and replacement of the lens function by an IOL. For many years most IOLs were made of poly (methylmethacrylate), a material with good optical characteristics and compatibility with the tissues of the eye. A disadvantage of PMMA is, however, that it is a very rigid material and the incision must be made large enough for implantation of the IOL. If the optical properties are not correctly matched, a need for a second IOL is required.

All incisions in the eye are accompanied by trauma, and so, although foldable lenses have been a great improvement, there is still a need for an IOL that can be adjusted without an additional incision. Complications of conventional IOL implantation, namely decentration and posterior capsular opacification, may also require adjustment.

Hydrogels are a class of materials that are very interesting for an injectable lens because they have the added advantage that their aqueous composition approximates that of the natural lens. Hydrogels can be made by crosslinking aqueous polymer or monomer/crosslinker solutions. Since monomers are often toxic, the use of polymers is preferred for applications in the eye. Polymers, to which a reactive group is attached, for example, an acrylate group, can be polymerized in the presence of water and form a hydrogel. However, the injectable lens may also not have the desired optical properties.

SUMMARY OF THE INVENTION

Embodiments of the present invention provide an improved ocular implant. This ocular implant includes an intraocular lens (IOL) and a number of haptics. The IOL passes optical energy. A microstructure within the IOL places the IOL under tension. The microstructure is operable to be broken in a controlled manner to release tension in the IOL and reshape the IOL. This may be done at any time post operatively and in conjunction with wavefront aberrometry to provide improved results. The haptics mechanically couple to the IOL in order to position and secure the IOL within the eye.

Other embodiments of the present invention provide a method to correct for visual impairment of aphakia. In one embodiment this involves removing a natural lens from an eye when the lens may be diseased, or damaged through accident. Next an IOL may be inserted within the eye and then secured and positioned with a number of haptics. A need for power adjustment of the in vivo IOL is determined. This may be done using wavefront aberrometry or other like diagnostic procedures. An implanted IOL having a controlled micro structure that places the IOL under tension can then be reshaped by adjusting the tension therein. This may be done by making appropriate changes to the micro structure of the IOL. These changes may involve using an external stimulus to reshape members, break crosslinks or induce cavities within the IOL.

Another embodiment of an IOL of this invention may have a predefined control structure wherein members of the structure may be adjusted in length to change the tension and reshape the IOL as desired. The changes to the controlled micro structure of the IOL are implemented with an external stimulus. Wavefront aberrometry and other diagnostic procedures may be applied after the adjustment to measure the effectiveness and determine if there is a need for further adjustment and, if so, whether or not the current micro structure will support that adjustment.

Other advantages of the present invention will become more apparent to one skilled in the art upon reading and understanding the detailed description of the preferred embodiments described herein with reference to the following drawings.

BRIEF DESCRIPTION OF THE DRAWINGS

For a more complete understanding of the present invention and the advantages thereof, reference is now made to the following description taken in conjunction with the accompanying drawings in which like reference numerals indicate like features and wherein.

DETAILED DESCRIPTION OF THE INVENTION

Preferred embodiments of the present invention are illustrated in the FIGs., like numerals being used to refer to like and corresponding parts of the various drawings.

An improved design for an ocular implant is provided. This ocular implant includes an intraocular lens (IOL) and a number of haptics. The IOL passes optical energy. A microstructure within the IOL places the IOL under tension. The microstructure is operable to be broken in a controlled manner to release tension in the IOL and reshape the IOL. This may be done at any time post operatively and with wavefront aberrometry to provide improved results. The haptics mechanically couple to the IOL in order to position and secure the IOL within the eye.

Figure 1:
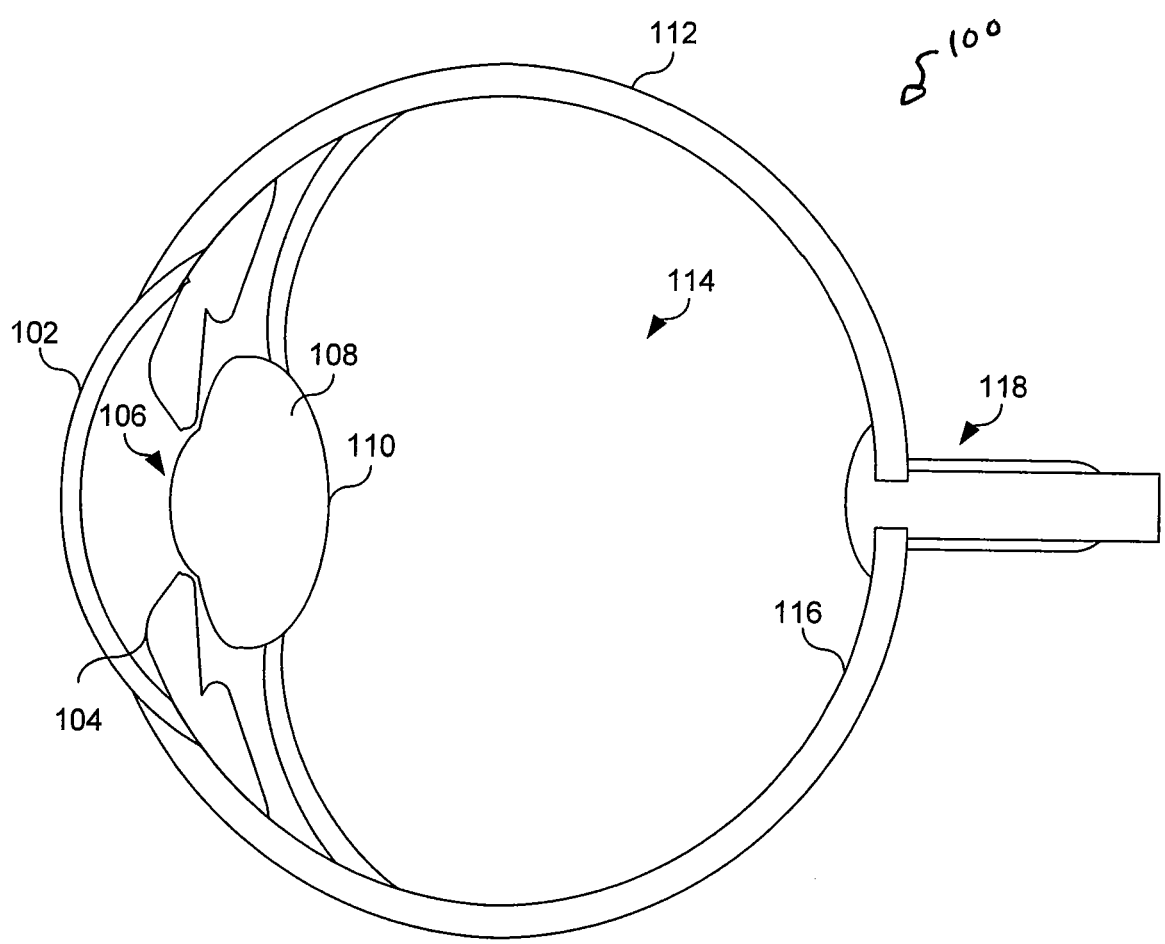
FIG. 1 illustrates the anatomy of the eye in which an intraocular lens (IOL) in accordance with embodiments of the present invention may be implanted.

FIG. 1 illustrates the anatomy of an eye into which the improved design for an ocular implant provided by the present invention may be implanted. Eye 100 includes cornea 102, iris 104, pupil 106, lens 108, lens capsule 110, zonules, ciliary body, sclera 112, vitreous gel 114, retina 116, macula, and optic nerve 118. Cornea 102 is a clear, dome-shaped structure on the surface of the eye that is transparent to visible light entering the eye. Iris 104, the colored part of the eye, is a muscle surrounding the pupil that relaxes and contracts to control the amount of light entering the eye. Pupil 106 is the round, central opening of the iris. Lens 108 is the structure inside the eye that helps to focus light on the retina. Lens capsule 110 is an elastic bag that envelops the lens, helping to control lens shape when the eye focuses on objects at different distances. Zonules are slender ligaments that attach the lens capsule to the inside of the eye, holding the lens in place. The Ciliary body is the muscular area attached to the lens that contracts and relaxes to control the size of the lens for focusing. Sclera 112 is the tough, outermost layer of the eye that maintains the shape of the eye. Vitreous gel 114 is located towards the back of the eyeball and helps to maintain the curvature of the eye. Retina 116 is a light-sensitive nerve layer in the back of the eye that receives light and converts it into signals to send to the brain. The macula is the area in the back of the eye that contains functions for seeing fine detail. Optic nerve 118 connects and transmits signals from the eye to the brain.

Figure 2:
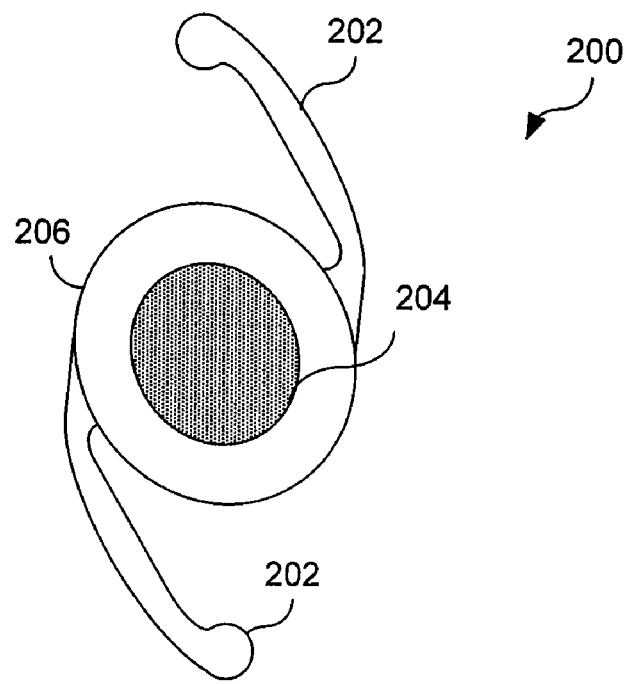
FIG. 2 depicts an IOL in accordance with embodiments of the present invention.

FIG. 2 depicts an IOL in accordance with embodiments of the present invention. IOL 200 is an artificial lens implanted in the eye to restore vision after a natural lens has been removed. The need for the IOL 200 may be due to cataract, disease or accidents. The lens of the IOL 200 may be convex on both sides (biconvex) and made of a soft plastic that can be folded prior to insertion, allowing placement through an incision smaller than the optic diameter of the lens. After surgical insertion into the eye, the lens gently unfolds to restore vision. The supporting arms (haptics) 202 provide for proper positioning of the IOL 200 within the eye.

IOL 200 may be positioned in the posterior chamber of the eye, replacing the natural lens 108. This position allows IOL 200 to correct the visual impairment of aphakia (absence of the natural lens 108). IOL 200 may have a biconvex optic that is shaped using a process designed to provide increased depth of focus. The IOL 200 may be used in adult patients with and without presbyopia who desire near, intermediate and distance vision with increased independence from glasses following cataract surgery. IOL 200 can provide good near, intermediate and distance vision with increased independence from glasses in patients who have undergone cataract surgery. IOL 200 delivers quality vision for various lighting situations. In brightly lit conditions, the central portion 204 sends light waves simultaneously to both near and distant focal points, while, in dimly lit conditions, the surrounding area 206 sends greater energy to distance vision.

Figure 3A:
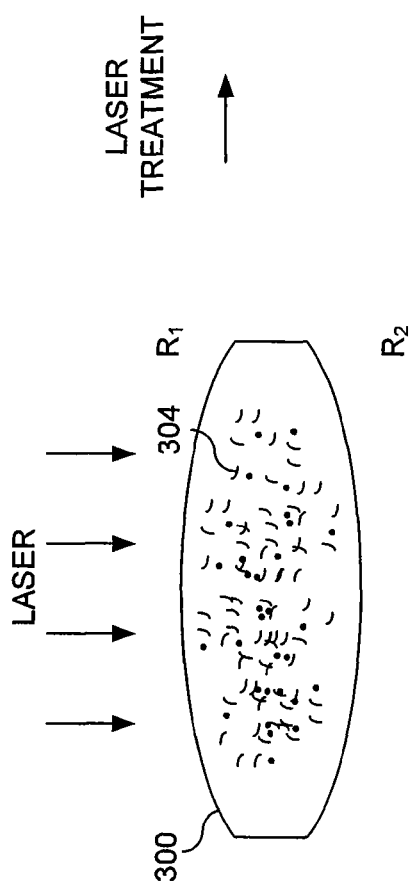
FIGS. 3A and 3B provide a cross section of an intraocular lens (IOL) operable to be adjusted in vivo in accordance with embodiments of the present invention.
Figure 3A:
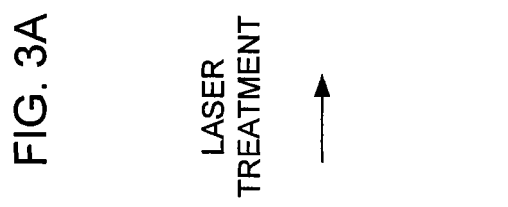
Figure 3B:
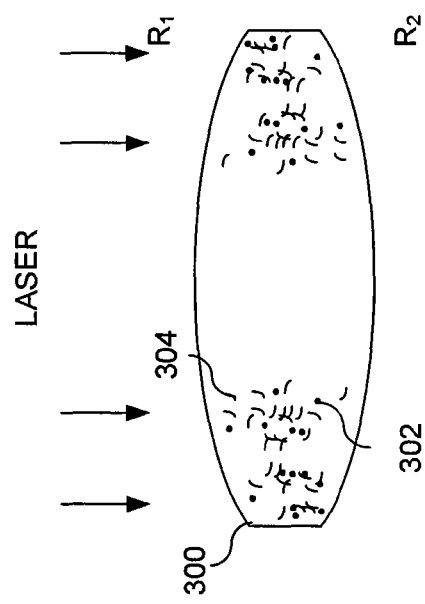

FIGS. 3A and 3B provide a cross section of an IOL 300 operable to be adjusted in vivo in accordance with embodiments of the present invention. IOL 300 can be made of a hydrogel type material or of a non-hydrogel material with controlled microstructure through crosslinks 304 or morphology. FIG. 3A shows a femtosecond laser directed towards the center of the IOL 300. Following laser treatment, FIG. 3A shows that the radius of curvature on both sides of the biconvex IOL has increased. FIG. 3A shows that IOL 300 flattens in response to the external stimulus. Similarly FIG. 3B shows a laser treatment applied to the periphery of IOL 300. Following laser treatment, FIG. 3B shows that the radius of curvature on both sides of the biconvex IOL 300 has decreased. FIG. 3B shows that IOL 300 gaining increased optical power in response to the external laser stimulus Currently there is no approved procedure or device for adjusting IOL power in vivo. The power adjustment provided in accordance with embodiments of the present invention may be accomplished using a femtosecond laser. A major advantage of IOL 300 and the power adjustment procedure provided in accordance with embodiments of the present invention is that the procedure is non-invasive and can be carried out to achieve a target refraction post-operatively. The femtosecond laser is used to create micro cavities 302 within the IOL, or to break up the cross-links 304, in order release the tension within the lens.

Creating micro cavities or micro perforations 302 at the center of the IOL 300 is expected to increase lens power and doing the same at the periphery of the IOL 300 is expected to flatten the curvature of the lens. The laser can also be applied to a specific region of the IOL 300 for cylinder correction, including correction for surgically induced astigmatism. As will be apparent to one skilled in the art, such regional correction could be used to make adjustments for a number of other aberrations in addition to cylindrical aberrations. The femtosecond laser is based on near-IR microsurgical lasers and has capability to create micron size implosions with low pulse energies of 2-4 micro joules, minimal acoustical shock wave, and without undesirable cavitations and bubbles.

Figure 4:
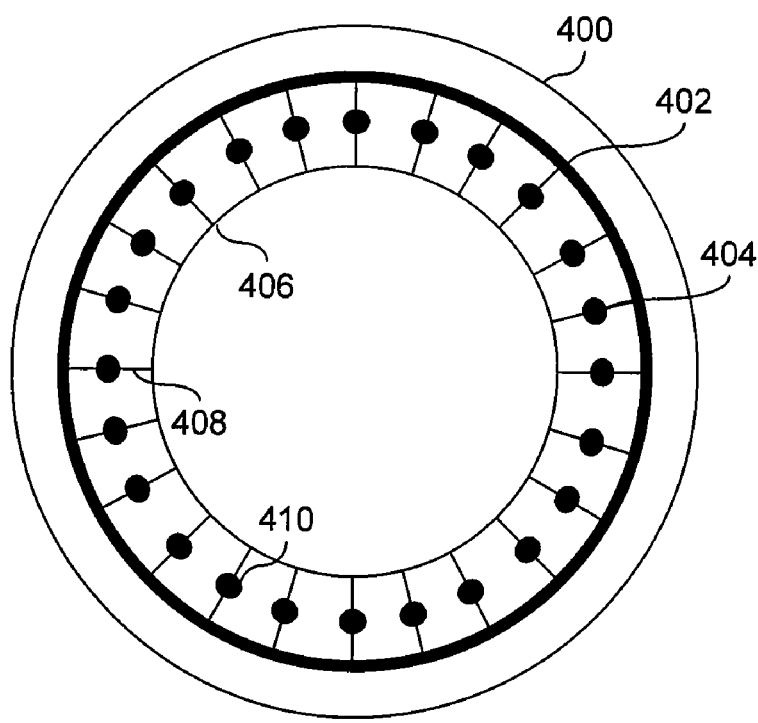
FIG. 4 depicts an IOL in accordance with embodiments of the present invention.

FIG. 4 depicts an IOL 400 in accordance with embodiments of the present invention. IOL 400 may be loaded with an Internal Structure 402 which may be deformed using a femtosecond laser to cause the power of IOL 400 to be adjusted. As shown in FIG. 4, IOL 400 is preloaded with a structure 402 which includes two concentric rings 404 and 406. Concentric Rings 404 and 406 have members 408 which may have localized regions or pockets of heat-absorbing material or dye 410.

Figure 5A:
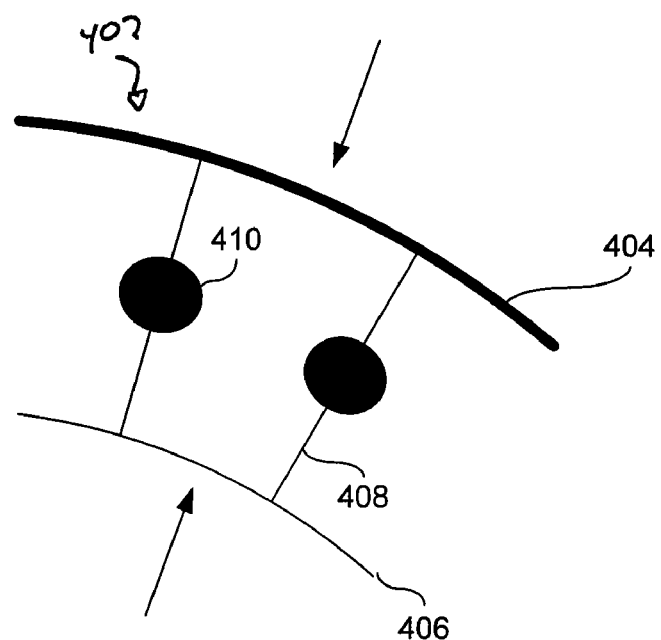
FIGS. 5A and 5B show how a laser may be applied to an internal structure of an IOL in order to effect changes in accordance with embodiments of the present invention.
Figure 5B:
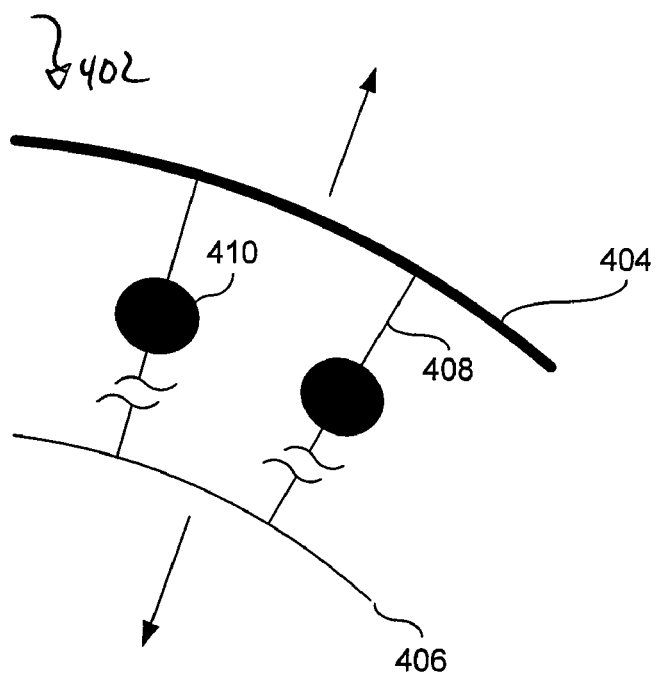

FIGS. 5A and 5B show how a laser may be applied to Structure 402 in order to effect changes. In FIG. 5A, heat-absorbing pockets 410, which may shrink when exposed to heat, increasing the stressor tension on inner ring 406 and outer ring 404, cause the IOL to be deformed. Similarly, as shown in FIG. 5B, links or members 408 may be broken using the femtosecond laser in order to release tension between concentric rings 406 and 408.

The embodiments of the IOL and procedure of this invention have many advantages over the prior art. For example, the non-invasive nature of the IOL power (sphere and cylinder) adjustment is a very desirable feature. Further, the IOL may be a fully cured lens without any significant unreacted monomer, oligomer or initiator. Further still, this power adjustment need not be performed within a limited postoperative period. Rather, the adjustment can be performed when a need arises for IOL power adjustment.

Another embodiment of the present invention relates to the use of ultrafast laser technology to perform ultrafine cutting to modify the shape of an IOL. The ultra short pulses in the range of pico to femto seconds at wavelengths in the vicinity of 1 micron can be used to ablate features into or materials away from an IOL to induce the shape of the IOL to change. Embodiments of the present invention use the ultrafast laser in a real-time application where a pseudophakic patient has their vision refined by using the ultra fast laser which is tracked to the moving eye. The laser performs intraocular surgical modification of a pre installed IOL designed to have its shape adapted based on the action of the femtosecond laser. The ultrafast pulses can be used to ablate or cut material from a specially preloaded controlled micro structure within the IOL, causing the IOL to deform in a desired manner. Such a microstructure was presented in FIGS. 3A, 3B, 4, 5A and 5B. A laser pulse duration of interest is from 100 fs to 10 picoseconds and the wavelength can range from 500 nm to 1.1 microns. Dyes can be used as part of the lens material to preferentially absorb the ultrafast laser pulses.

Embodiments of the present invention may employ the simultaneous, or at least contemporaneous, use of wavefront aberrometry to assess the aberration structure at all phases of the treatment from pre-implant through to the point in the procedure where the post-op aberrations are minimized by adjustment of the structure of the IOL. This approach does not require any alteration of the material properties of the IOL itself or require the optical portion of the IOL to be modified with the laser. Rather, the cutting or ablating action of the femtosecond laser can either be used to break load bearing members of the IOL that will allow the lens to flatten in one or more directions and take a more desirable shape OR it can be used to heat and shrink a mechanical element that will be able to induce a desired stress to the IOL, causing the lens to take a new steeper shape. Although the use of femtosecond lasers is specifically described, it will be apparent to one skilled in the art that other lasers or external stimuli may be suitable for performing the adjustments to the IOL described herein.

The possibility of making intraoperative adjustment to the shape of an IOL, and hence its optical power, when combined with the diagnostic power of wavefront aberrometry provides an opportunity to combine two successful technologies with a powerful new laser that has recently been introduced into the surgical armamentarium, namely the femtosecond laser. This type of laser is capable of penetrating the cornea without causing any significant heating or mechanical disruption, but can be focused to pinpoint accuracy into the anterior chamber to allow precision cutting (ablation) and or heating of materials within the anterior chamber. The width of the cut or ablation and the amount of associated debris can be very small, about 1-3 microns. Lower peak laser powers can be used to generate heat when the laser is interacting with a section of material that has been properly doped to permit preferential and very localized heating. In particular, an IOL can be pre-stressed to induce a specific spherical aberration in the lens that can be released as appropriate to shift the sign of the spherical aberration or induce compensating astigmatism as needed. This can be done to compensate for any residual corneal spherical aberration or astigmatism that was either pre-existing or induced by the surgery. The use of the femtosecond laser can be delayed in order to let the cornea completely heal from the IOL insertion procedure. This allows the lens to be adjusted in the presence of quiet and stable ocular optics.

Figure 6:
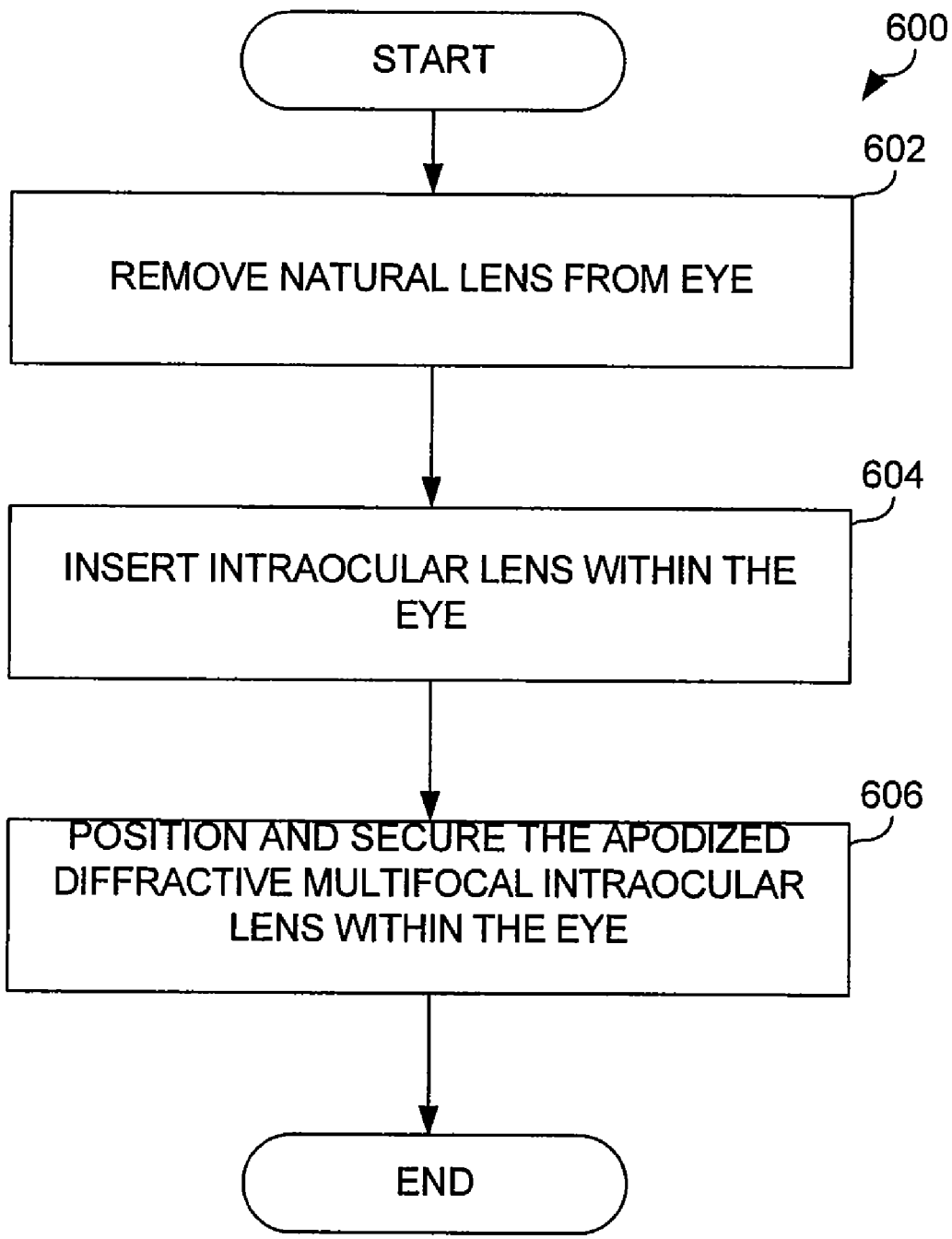
FIG. 6 provides a logic flow diagram of a method to correct for visual impairments such as aphakia of the eye in accordance with embodiments of the present invention.

FIG. 6 provides a logic flow diagram of an embodiment of a method to correct for visual impairments such as aphakia of the eye. Operation 600 begins with the removal of a natural lens from an eye in Step 602. The IOL, which may be a multi-focal IOL, may then be inserted within the eye. The lenses of the IOL may be convex on both sides (bi-convex) and made of a soft plastic that can be folded prior to insertion. This folding allows placement through a reduced-size incision wherein the incision is smaller than the optic diameter of the IOL. After surgical insertion into the eye in step 604, the IOL may gently unfold to restore vision. In Step 606, the IOL is positioned and secured within the eye. This may be done with the use of supporting arms (haptics) to provide for proper positioning of the IOL within the eye. Embodiments of the present invention may place or position the IOL in posterior chamber of the eye to replace the natural lens as shown in FIG. 1. This position allows the IOL to correct visual impairments such as the absence of a natural lens caused by disease or accident. The lens itself may be a multi-focal IOL as discussed previously. This allows patients with and without presbyopia who desire near intermediate and distant vision to experience independence from glasses following surgery, such as cataract surgery.

Figure 7:
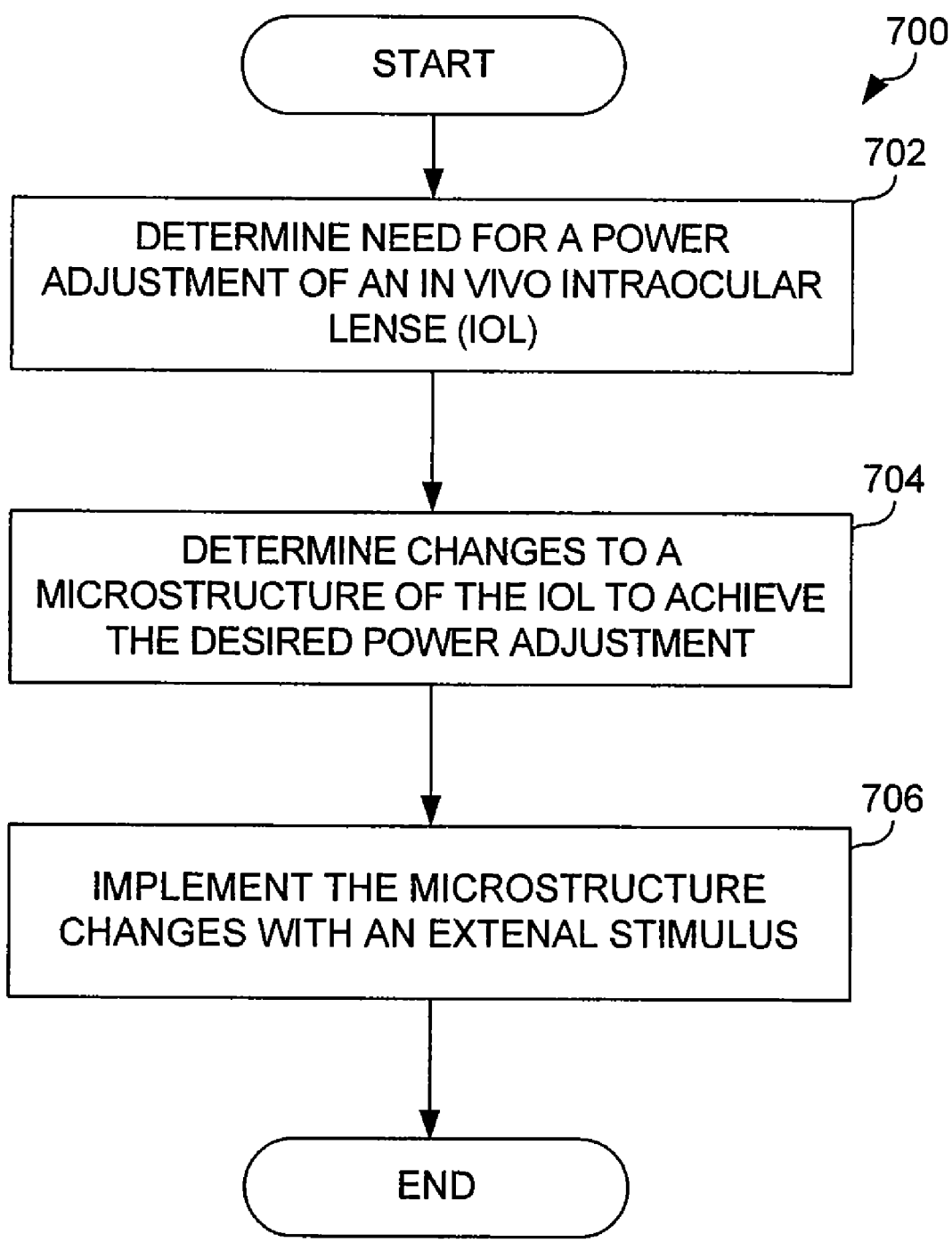
FIG. 7 provides a logic flow diagram of a method to power adjust an in vivo IOL to correct for visual impairments in accordance with embodiments of the present invention.

FIG. 7 provides a logic flow diagram of an embodiment of a method to power adjust an in vivo IOL to correct for visual impairments in accordance with embodiments of the present invention. This method allows power adjustments to be made to the IOL. Operation 700 begins at Step 702, wherein a need for power adjustment of an in vivo IOL is determined. This may be done using wavefront aberrometry or other like diagnostic procedures. If the IOL in place has a controlled micro structure that places the IOL under tension, it may be possible then to reshape the IOL by adjusting the tension therein. This may be done by making appropriate changes to the micro structure of the IOL. These changes are identified in Step 704. These changes may involve using an external stimulus, such as a femtolaser, to reshape members, break crosslinks or induce cavities within the IOL. Another embodiment may involve an IOL having a predefined control structure wherein members of the structure may be adjusted in length to change the tension and reshape the IOL as desired. In Step 706, the changes to the controlled micro structure of the IOL are implemented with an external stimulus. Wavefront aberrometry and other diagnostic procedures may be applied after the adjustment, either immediately or following a period of post surgical adaptation, to measure the effectiveness and determine if there is a need for further adjustment and, if so, whether or not the current micro structure will support that adjustment.

In summary, embodiments of the present invention provide an improved design for an ocular implant. This ocular implant includes an intraocular lens (IOL) and a number of haptics. The IOL passes optical energy. A microstructure within the IOL places the IOL under tension. The microstructure is operable to be broken in a controlled manner to release tension in the IOL and reshape the IOL. This may be done at any time post operatively and in conjunction with wavefront aberrometry to provide improved results. The haptics mechanically couple to the IOL in order to position and secure the IOL within the eye.

The IOL embodiments of this invention can be a multifocal IOL that passes optical energy in both photopic and mesopic conditions. The multifocal IOL may include both a diffractive region and a refractive region. The diffractive region may be a central region or optic zone of the lens that includes concentric steps of gradually varying step heights in order to allocate energy based on lighting conditions and activity in order to create a full range of quality vision, (i.e. near to distant). This allows conditions where the natural lens of the eye must be replaced to be corrected.

Embodiments of the present invention allow patients having visual impairment to have clear distance vision at smaller pupil conditions, i.e. photopic conditions, and have improved vision at larger pupil, i.e. mesopic conditions.

As one of average skill in the art will appreciate, the term "substantially" or "approximately", as may be used herein, provides an industry-accepted tolerance to its corresponding term. Such an industry-accepted tolerance ranges from less than one percent to twenty percent and corresponds to, but is not limited to, component values, integrated circuit process variations, temperature variations, rise and fall times, and/or thermal noise. As one of average skill in the art will further appreciate, the term "operably coupled", as may be used herein, includes direct coupling and indirect coupling via another component, element, circuit, or module where, for indirect coupling, the intervening component, element, circuit, or module does not modify the information of a signal but may adjust its current level, voltage level, and/or power level. As one of average skill in the art will also appreciate, inferred coupling (i.e., where one element is coupled to another element by inference) includes direct and indirect coupling between two elements in the same manner as "operably coupled". As one of average skill in the art will further appreciate, the term "compares favorably", as may be used herein, indicates that a comparison between two or more elements, items, signals, etc., provides a desired relationship. For example, when the desired relationship is that signal 1 has a greater magnitude than signal 2, a favorable comparison may be achieved when the magnitude of signal 1 is greater than that of signal 2 or when the magnitude of signal 2 is less than that of signal 1.

Although the present invention is described in detail, it should be understood that various changes, substitutions and alterations can be made hereto without departing from the spirit and scope of the invention as described by the appended claims.

What is claimed is:

1. An ocular implant, comprising:
    an intraocular lens (IOL) operable to pass optical energy, the IOL comprising a controlled microstructure, the microstructure operable to place the IOL under tension, wherein the microstructure is operable to adjust tension in a controlled manner in response to an external stimulus, the microstructure comprising:
        a first ring;
        a second ring, substantially concentric with the first ring;
        a plurality of members operable to link the first ring and the second ring; the members operable to change length in response to an external stimulus to adjust the tension within the IOL, each of the members comprising a pocket of heat-absorbing material that shrinks when exposed to heat to change the length of the respective member;
    a plurality of haptics coupled to the IOL operable to position the IOL within an eye.

2. The ocular implant of claim 1, wherein the IOL is operable to replace a natural lens of the eye.

3. The ocular implant of claim 1, wherein the IOL comprises:
    a diffractive region; and
    a refractive region.

4. The ocular implant of claim 3, wherein:
    the diffractive region is operable to pass optical energy simultaneously to both near and distant focal points in photopic conditions; and
    the refractive region is operable to pass optical energy to distance vision in mesopic conditions.

5. The ocular implant of claim 1, wherein the IOL comprises a biconvex optic.

6. The ocular implant of claim 1, wherein the microstructure is operable to controllably adjust tension to produce a change in a power of the IOL.

7. The ocular implant of claim 1, wherein the microstructure is operable to controllably adjust tension to produce a change in cylinder correction for the IOL.

8. An ocular implant, comprising:
    a multifocal intraocular lens (IOL) operable to pass optical energy in both photopic and mesopic conditions, the IOL comprises:
    a controlled microstructure, the microstructure operable to place the IOL under tension, wherein the microstructure is operable to adjust tension in a controlled manner in response to an external stimulus, the microstructure comprising:
        a first ring;
        a second ring, substantially concentric with the first ring;
        a plurality of members operable to link the first ring and the second ring; the members operable to change length in response to an external stimulus to adjust the tension within the IOL, each of the members comprising a pocket of heat-absorbing material that shrinks when exposed to heat to change the length of the respective member;
        a central diffractive region; and
        an outer refractive region;
    a plurality of haptics coupled to the IOL operable to position the IOL within an eye.

9. The ocular implant of claim 8, wherein the IOL is operable to replace a natural lens of the eye.

10. The ocular implant of claim 8, wherein:
    the diffractive region is operable to pass optical energy simultaneously to both near and distant focal points in photopic conditions; and
    the refractive region is operable to pass optical energy to distance vision in mesopic conditions.

11. The ocular implant of claim 8, wherein the IOL comprises a biconvex optic.

12. The ocular implant of claim 8, wherein the microstructure is operable to controllably adjust tension to produce a change in a power of the IOL.

13. The ocular implant of claim 8, wherein the microstructure is operable to controllably adjust tension to produce a change in cylinder correction for the IOL.

* * * * *